(12) United States Patent
Lerm et al.

(10) Patent No.: US 11,256,110 B2
(45) Date of Patent: Feb. 22, 2022

(54) SYSTEM AND METHOD OF UTILIZING COMPUTER-AIDED OPTICS

(71) Applicant: Alcon Inc., Fribourg (CH)

(72) Inventors: Dominik Lerm, Forchheim (DE); Stefan Schmid, Neuendettelsau (DE); Stefan Koch, Eckental (DE); Joerg Grampp, Vorra-Artelshofen (DE); Berndt Warm, Schwaig (DE); Peter Martin, Velden (DE)

(73) Assignee: Alcon Inc., Fribourg (CH)

( * ) Notice: Subject to any disclaimer, the term of this patent is extended or adjusted under 35 U.S.C. 154(b) by 293 days.

(21) Appl. No.: 16/677,392

(22) Filed: Nov. 7, 2019

(65) Prior Publication Data

US 2020/0201070 A1   Jun. 25, 2020

Related U.S. Application Data

(60) Provisional application No. 62/781,908, filed on Dec. 19, 2018.

(51) Int. Cl.
*G02C 7/02* (2006.01)
*A61B 3/00* (2006.01)
(Continued)

(52) U.S. Cl.
CPC ............ *G02C 7/027* (2013.01); *A61B 3/0025* (2013.01); *A61B 3/0091* (2013.01); *A61B 3/1015* (2013.01); *A61B 3/14* (2013.01)

(58) Field of Classification Search
CPC ..... G02C 7/027; A61B 3/0025; A61B 3/0091; A61B 3/1015; A61B 3/14; A61B 3/032; A61B 3/10
(Continued)

(56) References Cited

U.S. PATENT DOCUMENTS 6,270,221 B1   8/2001 Liang et al.
2003/0133074 A1   7/2003 Pettit et al.
(Continued)

FOREIGN PATENT DOCUMENTS

WO   2016149416 A1   9/2016

OTHER PUBLICATIONS

Larry N. Thibos, et al.; "Standards for Reporting the Optical Aberrations of Eyes"; Journal of Refractive Surgery; Sep./Oct. 2002; pp. S652-S660; vol. 18.
(Continued)

*Primary Examiner* — Mohammed A Hasan

(57) ABSTRACT

The disclosure provides a system that may provide a virtual object at a first virtual distance to an eye of a patient; may provide a first light wave to the eye; may receive a first perturbed light wave, based at least on the first light wave, from the eye; may determine first optical corrections based at least on the first perturbed light; may provide the virtual object at a second virtual distance to the eye; after providing the virtual object at the second virtual distance, may provide a second light wave to the eye; may receive a second perturbed light wave, based at least on the second light wave, from the eye; may determine second optical corrections based at least on the second perturbed light; and may determine a corrective optical solution for the eye based at least on the first optical corrections and the second optical corrections.

20 Claims, 9 Drawing Sheets

(51) Int. Cl.
*A61B 3/10* (2006.01)
*A61B 3/14* (2006.01)

(58) Field of Classification Search
USPC .......................................................... 351/211
See application file for complete search history.

(56) References Cited

U.S. PATENT DOCUMENTS

| | | | |
|---|---|---|---|
| 2006/0142908 A1* | 6/2006 | Grier | G07C 5/0825 |
| | | | 701/31.4 |
| 2008/0291395 A1* | 11/2008 | Dai | A61B 3/107 |
| | | | 351/205 |
| 2009/0153796 A1 | 6/2009 | Rabner | |
| 2011/0149239 A1* | 6/2011 | Neal | G02C 7/04 |
| | | | 351/205 |

OTHER PUBLICATIONS

James C. Wyant; "Zernike Polynomials"; ZernikePolynomialsfortheWeb.nb; https://authorzilla.com/EL2aX/zernikepolynomialsfortheweb-nb.html; 2003; pp. 1-33.

* cited by examiner

SYSTEM AND METHOD OF UTILIZING COMPUTER-AIDED OPTICS

BACKGROUND

Field of the Disclosure

This disclosure relates to eye exams and more particularly to utilizing computer-aided optics in performing eye exams.

Description of the Related Art

In the past, medical personnel have utilized refraction to obtain information for a prescription for spectacles and/or contact lenses. Usually, a patient is twenty feet from a chart and looks through a phoropter, which can allow the medical personnel move lenses of different strengths in front of the eyes of the patient. This examination can also help the medical personnel in diagnosing presbyopia, hyperopia, myopia, and/or astigmatism. Also, in the past, medical personnel have utilized visual acuity testing, which can measure how well a patient can see at near and far distances. The medical personnel can also perform a visual field test, which can measure peripheral vision. These tests can require a variety of instruments. Additionally, a patient was present in the same exam room as the medical personnel.

SUMMARY

The present disclosure provides a system able to provide a virtual object at a first virtual distance to an eye of a patient. For example, the system may include a projector. The projector may provide the virtual object at the first virtual distance to the eye of the patient. The system may further provide a first light wave to the eye of the patient and may receive a first perturbed light wave, based at least on the first light wave, from the eye of the patient. For example, the system may include a wavefront sensor. The wavefront sensor may receive the first perturbed light wave, based at least on the first light wave, from the eye of the patient. The system may further determine first optical corrections based at least on the first perturbed light. For example, the system may include a computer system. The computer system may determine the first optical corrections based at least on the first perturbed light. The wavefront sensor may determine the first optical corrections based at least on the first perturbed light. The system may further provide the virtual object at a second virtual distance, different from the first virtual distance, to the eye of the patient. The projector may provide the virtual object at the second virtual distance to the eye of the patient. The system may further, after providing the virtual object at the second virtual distance to the eye of the patient, provide a second light wave to the eye of the patient. The system may further receive a second perturbed light wave, based at least on the second light wave, from the eye of the patient. The wavefront sensor may receive the second perturbed light wave, based at least on the second light wave, from the eye of the patient. The system may further determine second optical corrections based at least on the second perturbed light. The computer system may determine the second optical corrections based at least on the second perturbed light. The wavefront sensor may determine the second optical corrections based at least on the second perturbed light. The system may further determine a corrective optical solution for the eye of the patient based at least on the first optical corrections and the second optical corrections.

The system may further determine first multiple polynomials based at least on the first perturbed light when the system determines the first optical corrections based at least on the first perturbed light. The system may further determine second polynomials, different from the first polynomials, based at least on the second perturbed light when the system determines the second optical corrections based at least on the second perturbed light. For example, a polynomial of the first polynomials may differ from a polynomial of the second polynomials by at least one coefficient value.

The system may include a deformable mirror. The system may further configure the deformable mirror based at least on the corrective optical solution for the eye of the patient. The system may further provide, via the deformable mirror, the virtual object to the eye of the patient. For example, an optical path between the projector and the eye of the patient may include the deformable mirror. The system may further receive input from the patient that indicates if the virtual object is acceptably viewed by the eye of the patient.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) provide a virtual object at a first virtual distance to an eye of a patient; ii) provide a first light wave to the eye of the patient; iii) receive a first perturbed light wave, based at least on the first light wave, from the eye of the patient; iv) determine first optical corrections based at least on the first perturbed light; v) provide the virtual object at a second virtual distance, different from the first virtual distance, to the eye of the patient; vi) after providing the virtual object at the second virtual distance to the eye of the patient, provide a second light wave to the eye of the patient; vii) receive a second perturbed light wave, based at least on the second light wave, from the eye of the patient; viii) determine second optical corrections based at least on the second perturbed light; ix) determine a corrective optical solution for the eye of the patient based at least on the first optical corrections and the second optical corrections; x) configure a deformable mirror based at least on the corrective optical solution for the eye of the patient; xi) provide, via the deformable mirror, the virtual object to the eye of the patient; and xii) receive input from the patient that indicates if the virtual object is acceptably viewed by the eye of the patient.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
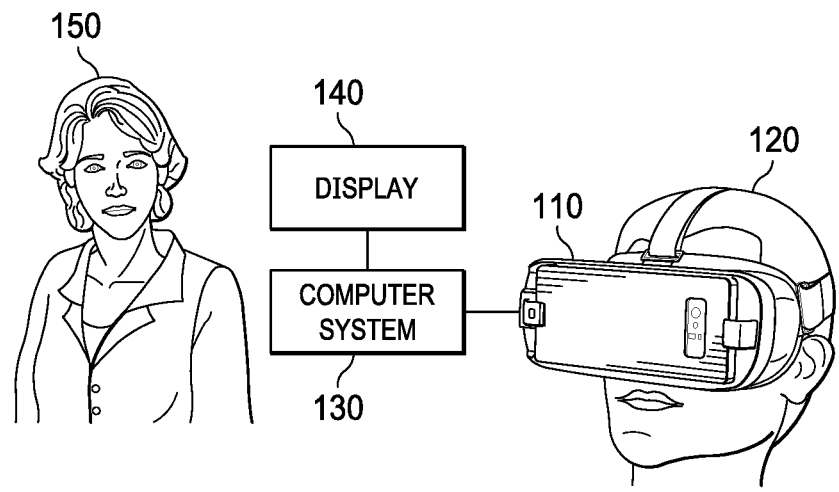
FIG. 1A illustrates an example of a diagnostic system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

A diagnostic system may include a projector that may provide one or more images to an eye of a patient. For example, the projector may include a display. The one or more images may be distorted in a targeted manner such that the patient perceives the one or more images as defect-free or almost defect-free. The diagnostic system may be utilized in determining a wavefront measurement of a refraction including higher order visual defects, a visual acuity examination, a stimulus perception, a resulting reaction from the stimulus perception, an examination of the field of vision (perimetry), a refraction measurement, color vision, contrast vision, and/or three dimensional vision, among others.

The diagnostic system may include one or more portions of a virtual reality (VR) system. In one example, the adaptive optics of the diagnostic system may correct optical aberrations of an eye of a patient, and the one or more portions of the VR system may playback corrected wavefronts from different environmental scenarios (e.g., light conditions, colors, contrasts, etc.) to the eye of the patient. The patient may interactively experience expected results. In a second example, an eye tracking system of the diagnostic system may be utilized in examining one or more reactions to one or more stimuli. Situations (e.g., walking, running, driving a car, reading, etc.) may be examined in a targeted fashion. The diagnostic system may be utilized in facilitating one or more objective determinations of visual acuity. In a second example, a diagnostic system may be utilized in training one or more solution approaches (e.g., multi-focus, monovision, etc.). In another example, the diagnostic system may be utilized with an examination that may include a visual acuity examination associated one or more everyday scenarios. One or more scenarios may include reading a newspaper, performing office work, color variations, brightness variations, driving during daytime hours, driving during nighttime hours, and an eye chart, among others.

Adaptive optics may be utilized with head mounted displays (HMDs). For example, a head mounted display (HMD) with adaptive optics may be utilized in a diagnostic system. The diagnostic system may be utilized in an examination of one or more eyes of a patient. The adaptive optics may include one or more deformable mirrors that may correct one or more incoming wavefronts. For example, a diagnostic system may include one or more wavefront sensors. A wavefront sensor may determine one or more measurements from one or more wavefronts and may provide data associated with the one or more measurements to a computer system. The computer system may control one or more deformable mirrors based at least on the data associated with the one or more measurements. In one example, the computer system may control the one or more deformable mirrors to correct one or more aberrations of an eye of a patient. In another example, the wavefront sensor may control the one or more deformable mirrors to correct one or more aberrations of an eye of a patient.

The diagnostic system may display a "virtual examination room". For example, the diagnostic system may include one or more portions of a VR system that may display "virtual examination room" to a patient. The diagnostic system may include adaptive optics. For example, the adaptive optics may include a mirror that may guide images to a retina of a patient. One or more aberrations of the eye of the patient may be compensated by a position of the mirror, such that the patient may perceive a sharp image or a sharper image. The diagnostic system may include an eye tracking system. For example, the diagnostic system may determine, via the eye tracking system, one or more positions that may be "looked at" by the patient. An image resolution and/or an image correction in a virtual space may be predetermined in a targeted fashion for a location where the patient looks. For example, the VR examination room may be presented at a lower resolution and/or with a poorer wavefront correction in one or more peripheral regions of vision of the patient. For example, the patient may experience vision without a wavefront aberration in one or more everyday scenarios. The eye tracking system may be utilized to determine, for the patient, a distance to an object in the VR space by way of adaptive optics of the diagnostic system.

The VR system may include a form of spectacles or a HMD. For example, spectacles or a HMD may facilitate interaction and/or examination utilizing the diagnostic system by determining one or more movements a head of the patient. The patient may move his or her head to interact with the diagnostic system. The diagnostic system may be integrated and/or implemented via a desktop computer system, a laptop computer system, or a tablet computer system, among others. For example, the diagnostic system may be integrated and/or implemented via a desktop computer system, a laptop computer system, or a tablet computer system, among others, without spectacles or a HMD. One or more VR features may be utilized when utilizing a desktop computer system or a laptop computer system without spectacles or a HMD.

Utilizing the diagnostic system, the patient may experience one or more treatment results. For example, the patient may experience one or more treatment results, via the diagnostic system, before treatment is provided and/or implemented. The diagnostic system may be utilized in preoperative and/or postoperative data collection. The diagnostic system may be utilized in testing and/or training with one or more treatment options. For example, the one or more treatment options may include one or more of presbyopia correction, multi-focus, monovision, adapted asphericity, and different reflections in both eyes, among others.

Turning now to FIG. 1A, an example of a diagnostic system is illustrated. As shown, a diagnostic system 110 may be utilized with a patient 120. For example, diagnostic system 110 may include a HMD. Diagnostic system 110 may be utilized in examining and/or diagnosing one or more eyes of patient 120. For example, diagnostic system 110 may include one or more image projectors, one or more optics, one or more adaptive optics, one or more eye trackers, and/or one or more wavefront sensors, among others. Diagnostic system 110 may be utilized in determining higher-order aberrations (HOAs). For example, diagnostic system 110 may include an aberrometer that may determine vision errors by measuring how light waves travel through an optical system of an eye associated with patient 120. HOAs may include more subtle and/or complex refractive errors than nearsightedness, farsightedness, and/or astigmatism, among others. HOAs may include one or more of coma, spherical aberration, and trefoil, among others. HOAs may cause difficulty with halos, glare, blurring, starburst patterns, double vision (diplopia), and/or seeing at night, among others.

As illustrated, diagnostic system 110 may be communicatively coupled to a computer system 130. As shown, a display 140 may be coupled to computer system 130. Although display 140 is illustrated as external to computer system 130, computer system 130 may include display 140. A medical professional 150 may utilize computer system 130 to control diagnostic system 110. Medical professional 150 may be at the same physical location as patient 120. In one example, medical professional 150 may be at the same room as patient 120. In another example, medical professional 150 may be at the same medical facility as patient 120. Medical professional 150 may not be at the same physical location as patient 120. For example, medical professional 150 may be at a first geographic location, and patient 120 may be at a second geographic location, different from the first geographic location. The first geographic location may be at a distance from the second geographic location.

Figure 1B:
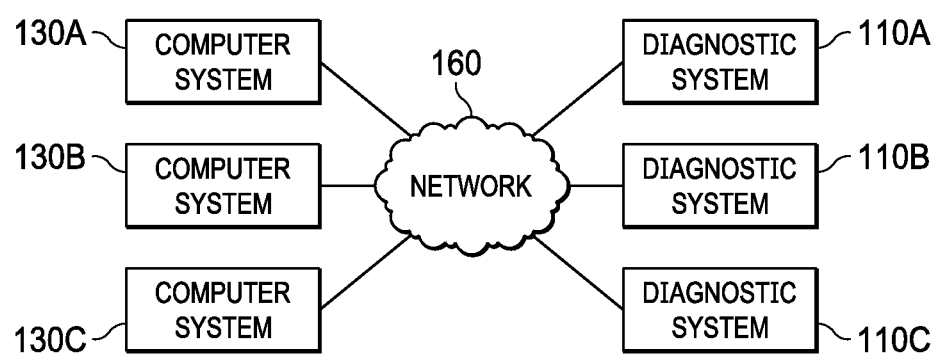
FIG. 1B illustrates an example of diagnostic systems and computer systems communicatively coupled to a network.

Turning now to FIG. 1B, an example of diagnostic systems and computer systems communicatively coupled to a network is illustrated. At shown, diagnostic systems 110A-110C may be communicatively coupled to a network 160. As illustrated, computer systems 130A-130C may be communicatively coupled to network 160. For example, one or more of computer systems 130A-130C may be located remotely from one or more of diagnostic systems 110A-110C. Network 160 may include a wired network, a wireless network, an optical network, or a combination of the foregoing, among others. Network 160 may include and/or be coupled to various types of communications networks. For example, network 160 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

Figure 1C:
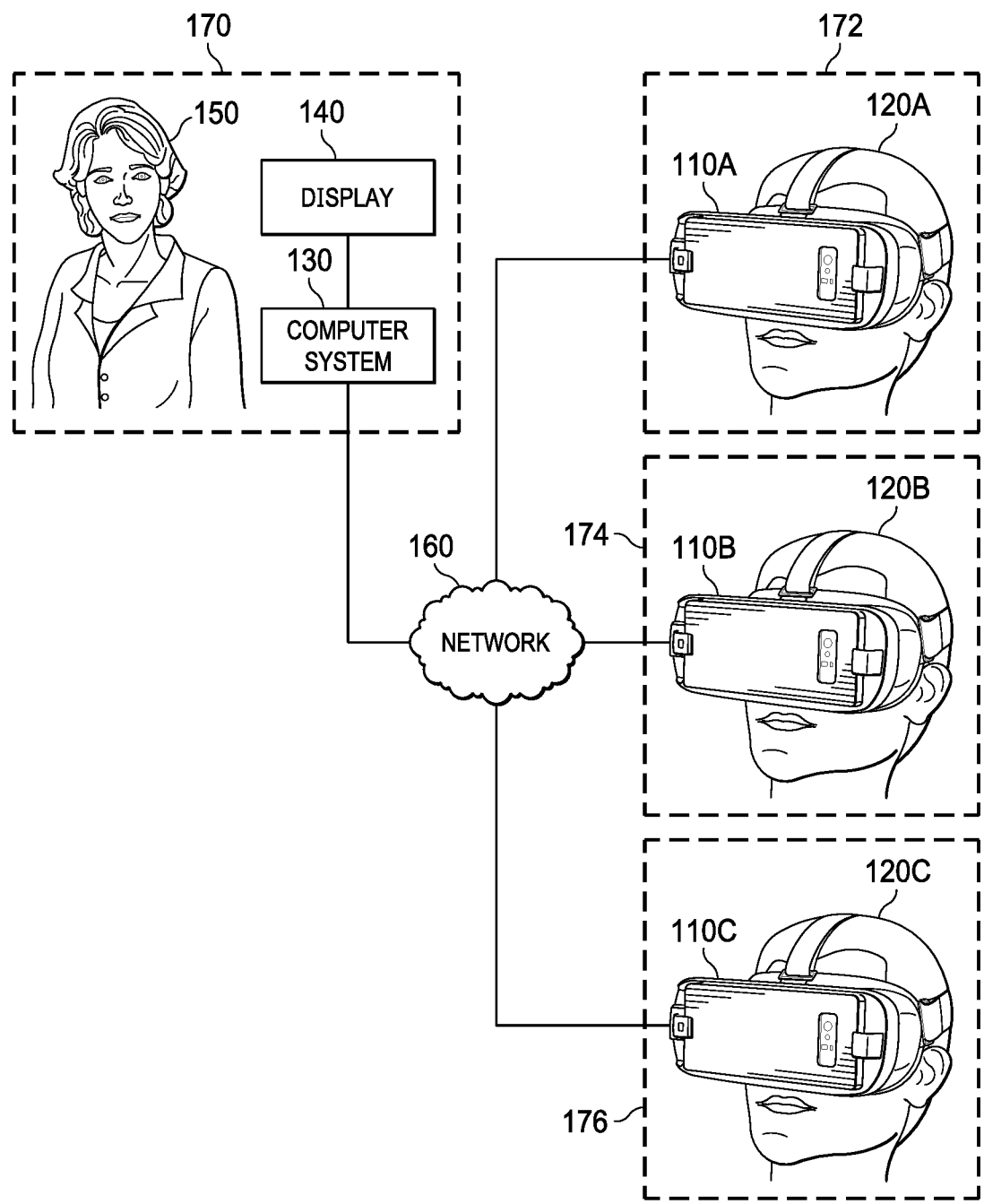
FIG. 1C illustrates an example of diagnostic systems at physical locations.

Turning now to FIG. 1C, an example of diagnostic systems at physical locations is illustrated. As shown, medical professional 150 and computer system 130 may be located at a physical location 170. As illustrated, diagnostic device 110A and patient 120A may be located at a physical location 172. As shown, diagnostic device 110B and patient 120B may be located at a physical location 174. As illustrated, diagnostic device 110C and patient 120C may be located at a physical location 176. For example, medical professional 150 may utilize computer system 130 to control diagnostic devices 110A-110C at respective physical locations 172-176. A physical location may include a geographic location.

Two of more of physical locations 172-176 may be different physical locations of a medical facility. In one example, two of more of physical locations 172-176 may be different rooms of the medical facility. In another example, two of more of physical locations 172-176 may be different chairs of the medical facility. Two of more of physical locations 172-176 may be different physical locations of a geographic region. In one example, two of more of physical locations 172-176 may be meters apart. In another example, two of more of physical locations 172-176 may be kilometers apart. Location 170 may be at any distance from a location of locations 172-176. Although not specifically illustrated, location 170 may include one or more of locations 172-176. Although not specifically illustrated, any location of location of locations 172-176 may include other one or more of locations 172-176.

Figure 2A:
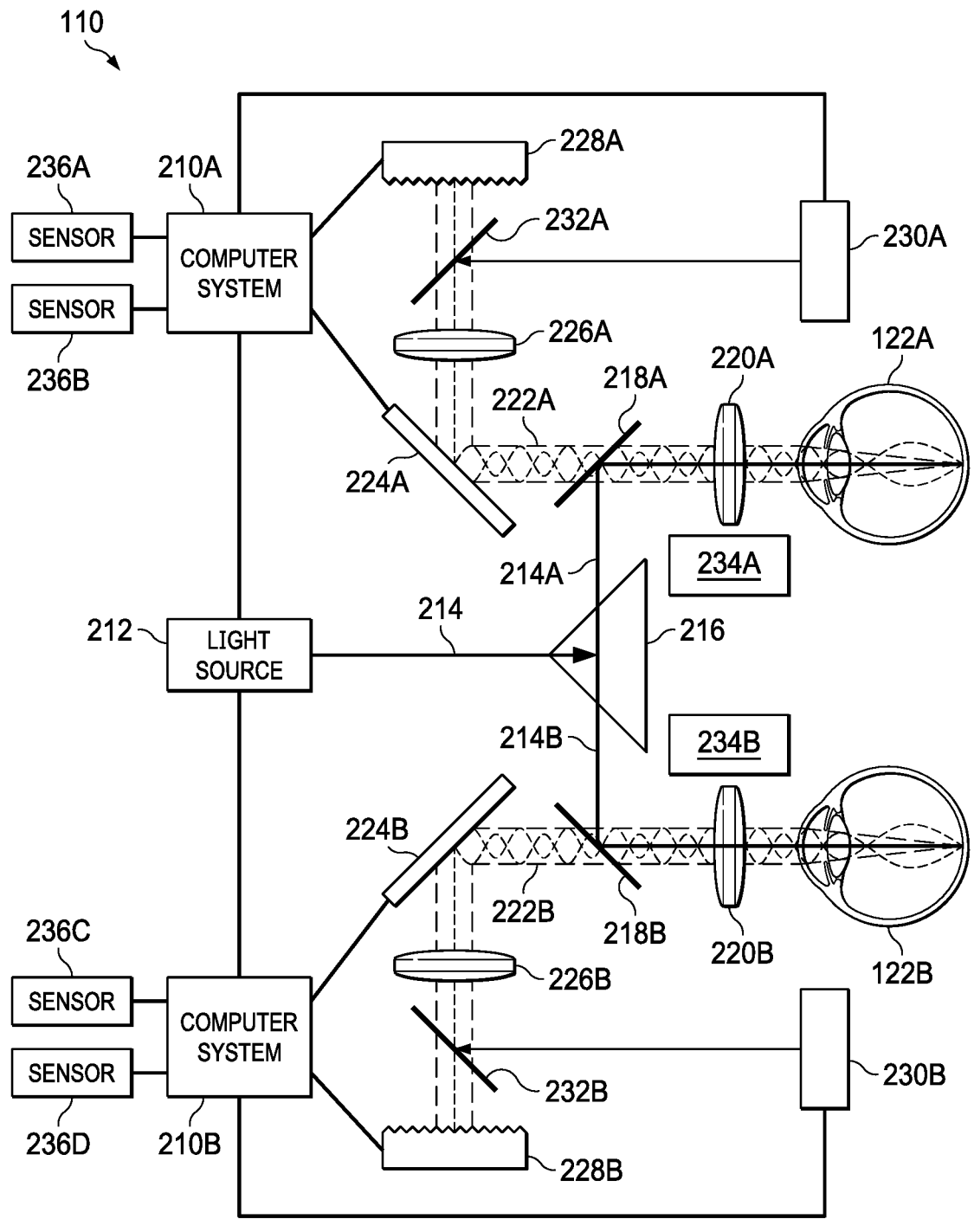
FIG. 2A illustrates a second example of a diagnostic system.

Turning now to FIGS. 2A, a second example of a diagnostic system is illustrated. As shown, diagnostic system 110 may include computer systems 210A and 210B. Computer systems 210A and 210B may be combined into a single computer system. As illustrated, diagnostic system 110 may include a light source 212. As shown, light source 212 may be communicatively coupled to computer systems 210A and 210B. For example, one or more of computer systems 210A and 210B may control light source 212. Light source 212 may emit light 214. A reflector 216 may split light 214 into light 214A and 214B. For example, reflector 216 may include a beam splitter.

As illustrated, light 214A may be reflected by a reflector 218A. As shown, light 214B may be reflected by a reflector 218B. As illustrated, light 214A may pass through a lens 220A. As shown, light 214B may pass through a lens 220B. As illustrated, light 214A may enter an eye 122A. For example, eye 122A may be an eye of patient 120. As shown, light 214B may enter an eye 122B. For example, eye 122B may be an eye of patient 120.

As illustrated, perturbed light 222A may travel through lens 220A. As shown, perturbed light 222B may travel through lens 220B. As illustrated, perturbed light 222A may be reflected by a deformable mirror 224A. For example, computer system 210A may control deformable mirror 224A. As shown, perturbed light 222B may be reflected by a deformable mirror 224B. For example, computer system 210B may control deformable mirror 224B.

As illustrated, perturbed light 222A may travel through a lens 226A. As shown, perturbed light 222B may travel through a lens 226B. As illustrated, a wavefront sensor 228A may receive perturbed light 222A. As shown, a wavefront sensor 228B may receive perturbed light 222B. Wavefront sensor 228A may provide first data, associated with perturbed light 222A, to computer system 210A. Wavefront sensor 228B may provide first data, associated with perturbed light 222B, to computer system 210B.

A wavefront sensor 228 may be utilized in determining HOAs. For example, wavefront sensor 228 may determine HOAs via one or more distortions acquired by a wavefront of light as it passes through an eye 122. For example, a uniform wavefront of light rays passing through an eye 122 may acquire three-dimensional, distorted shapes. More than sixty different wavefront shapes and/or aberrations may be possible. For example, a wavefront may be represented by one or more mathematical expressions. The one or more mathematical expressions may include Zernike polynomials, among others. For example, a polynomial may describe an aberration existing at a specific point on a wavefront of light, after it passes through eye 122. For example, a sum of polynomials may describe of aberrations or refractive errors associated with eye 122. For example, coefficients of polynomials may describe of aberrations or refractive errors associated with eye 122. The polynomials may form a topographic map associated with eye 122. For example, the polynomials associated with eye 122 may provide a representation of a shape of an aberrated wavefront associated with eye 122. Wavefront sensor 228 may determine one or more coefficients of polynomials associated with a received wavefront. Computer system 210 may determine one or more coefficients of polynomials associated with a received wavefront.

Although not specifically illustrated, wavefront sensor 228 may be communicatively coupled to deformable mirror 224. For example, wavefront sensor 228 may provide configuration information to deformable mirror 224. Deformable mirror 224 may implement one or more adjustments based at least on the configuration information. For example, the configuration information may be based at least on polynomials associated with a received wavefront.

A wavefront map may describe one or more aberrations affecting an eye 122. A wavefront map may be utilized in determining a vision correction of an eye 122. For example, a vision correction of an eye 122 may include one or more of intraocular lenses, refractive surgery, contact lenses, and glasses, among others. An example of refractive surgery may include laser-assisted in situ keratomileusis (LASIK) surgery.

Computer system 210A may control deformable mirror 224A to correct perturbed light 222A. In one example, computer system 210A may control deformable mirror 224A to correct perturbed light 222A such that perturbed light 222A no longer perturbed. In another example, computer system 210A may control deformable mirror 224A to correct perturbed light 222A such that a perturbation of perturbed light 222A is reduced. Computer system 210B may control deformable mirror 224B to correct perturbed light 222B. In one example, computer system 210B may control deformable mirror 224B to correct perturbed light 222B such that perturbed light 222B no longer perturbed. In another example, computer system 210B may control deformable mirror 224B to correct perturbed light 222B such that a perturbation of perturbed light 222B is reduced.

A projector 230A may provide first one or more images. For example, projector 230A may include a first display that may display the first one or more images. A reflector 232A may reflect the first one or more images to deformable mirror 224A. Deformable mirror 224A may alter the first one or more images. The altered first one or more image may be provided to eye 122A. Computer system 210A may utilize projector 230A and deformable mirror 224A to provide one or more first altered images to eye 122A.

A projector 230B may provide second one or more images. For example, projector 230B may include a second display that may display the second one or more images. A reflector 232B may reflect the second one or more images to deformable mirror 224A. Deformable mirror 224B may alter the second one or more images. The altered second one or more image may be provided to eye 122B. Computer system 210B may utilize projector 230B and deformable mirror 224B to provide one or more second altered images to eye 122B. One or more of the first one or more images may be the same as one or more of the second one or more images. For example, projector 230A may provide the same image one or more images as projector 230B may provide. Projector 230A may concurrently provide the same image one or more images as projector 230B may provide. Projector 230A may provide the same image one or more images as projector 230B may provide, but at different times. Although projector 230 is illustrated as being flat, projector 230 may include any shape. For example, projector 230 may be curved. Projector 230 may be curved based at least on one or more design specifications of diagnostic system 110. For example, diagnostic system 110 may not exceed one or more dimensions and/or one or more volumes, among others.

Utilizing a projector 230 to project one or more images to eye 122 and utilizing optics of diagnostic system 110, a distance to an object in one or more images may be configured. For example, computer system 210 may configure a distance to an object in the one or more images that may be displayed by projector 230. Utilizing projector 230 to project one or more images to eye 122, one or more alterations to the one or more images may be configured. For example, computer system 210 may configure one or more alterations to the one or more images that may be displayed by projector 230. Diagnostic system 110 may configure a distance to a virtual object utilizing one or more of projector 230, lens 220, deformable mirror 224, and lens 226, among others.

As illustrated, diagnostic system 110 may include eye trackers 234A and 234B. Although not specifically illustrated, eye trackers 234A and 234B may be coupled to computer systems 210A and 210B, respectively. An eye tracker 234 may include one or more sensors that may be utilized in determining where an eye 122 is focused. In one example, eye tracker 234 may provide infrared light or near infrared light to eye 122. In another example, eye tracker 234 may receive reflections of infrared light or near infrared light. Eye tracker 234 may determine a focus, a gaze point, and/or a position, among others, of eye 122 based at least on received reflections of infrared light or near infrared light.

Eye tracking may include a process of measuring at least one of a point of gaze (e.g., where eye 122 is looking) and a motion of eye 122. For example, eye tracker 234 may include a system that may determine one or more positions of eye 122 and/or one or more movements of eye 122. Eye tracker 234 may determine one or more positions of eye 122 and/or one or more movements of eye 122 in a non-contact fashion. For example, eye tracker 234 may project light onto eye 122 and receive reflections of the light from eye 122. Eye tracker 234 may determine one or more positions of eye 122 and/or one or more movements of eye 122 in a contact fashion. For example, eye tracker 234 may include electrodes that may contact skin of patient 120 around eye 122. One or more electrical potentials may be determined via the electrodes. For example, one or more positions of eye 122 and/or one or more movements of eye 122 may be determined via the one or more electrical potentials.

Eye tracker 234 may include an image acquisition device (e.g., a camera). For example, the image acquisition device may acquire one or more images of eye 122 as eye 122 views one or more objects and/or images and/or as eye 122 is subjected to one or more stimuli. Eye tracker 234 and/or computer system 210 may determine one or more positions of eye 122 and/or one or more movements of eye 122 based at least on the images from the image acquisition device. Eye tracker 234 may determine one or more pupil diameter measurements of eye 122. For example, diagnostic system 110 may determine one or more one or more pupil diameter reactions to one or more changes in light intensities and/or reactions to one or more changes in light colors, among others.

As illustrated, diagnostic system 110 may include sensors 236A-236D. Sensors 236A and 236B may be communicatively coupled to computer system 210A. Sensors 236C and 236D may be communicatively coupled to computer system 210B. In one example, a sensor 236 may include an electronic accelerometer. In a second example, a sensor 236 may include an electronic gyroscope. In a third example, a sensor 236 may include a microphone. In a fourth example, a sensor 236 may include an electronic magnetometer. In a fifth example, a sensor 236 may include an electronic thermometer. In a sixth example, a sensor 236 may include an electronic pressure sensor. In a seventh example, a sensor 236 may include an electronic altimeter. In an eighth example, a sensor 236 may include an electronic compass. In a ninth example, a sensor 236 may include an electronic light sensor. In another example, a sensor 236 may include an electronic global positioning system (GPS) receiver device.

Diagnostic system 110 may determine one or more issues with an eye 122 via an eye tracker 234. For example, diagnostic system 110 may determine that eye 122 is compensating for a retinal issue based at least on information from tracker 234. Diagnostic system 110 may adjust optics of diagnostic system 110 based at least on information from tracker 234.

Computer system 210 may implement a method that performs one or more diagnostic tests. For example, computer system 210 may store one or more results of the one or more diagnostic tests. Computer system 210 may provide the one or more results. Computer system 210 may provide the one or more results to computer system 130. In one example, computer system 210 may provide the one or more results to computer system 130 within a few seconds. In a second example, computer system 210 may provide the one or more results to computer system 130 within a few days. In another example, computer system 210 may provide the one or more results to computer system 130 within a few weeks. The amount of time that transpires between computer system 210 receiving and/or determining the one or more results and computer system providing the one or more results to computer system 130 may be arbitrary. For example, computer system 210 may not be coupled to network 160 while computer system 210 receives and/or determines the one or more results. Computer system 210 may coupled to network 160 after computer system 210 receives and/or determines the one or more results. In one example, diagnostic system 110 may be utilized in a waiting room of a medical facility. In another example, diagnostic system 110 may be utilized in a tour of one or more rural areas and/or one or more remote locations.

Figure 3A:
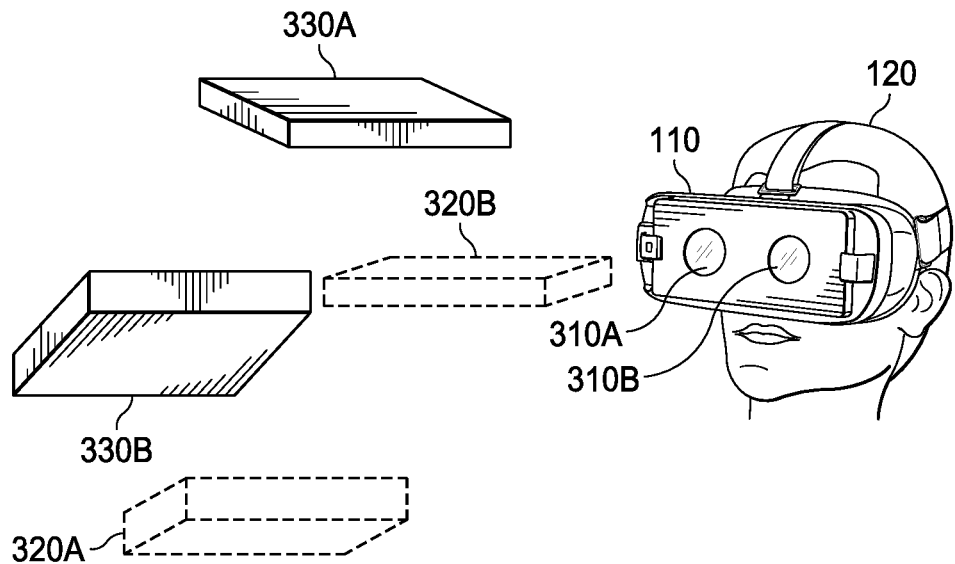
FIG. 3A illustrates another example of a diagnostic system.

Turning now to FIG. 3A, another example of a diagnostic system is illustrated. As shown, diagnostic system 110 may include transparent areas 310A and 310B. For example, transparent areas 310A and 310B may permit light to pass through to eyes 122A and 122B, respectively. Diagnostic system 110 may provide one or more images from one or more projectors 230A and 230B and may permit light to pass through to eyes 122A and 122B. For example, diagnostic system 110 may include one or more functionalities and/or one or more structures of an augmented reality system. As illustrated, objects 320A and 320B may be images that diagnostic system 110 may display to one or more eyes 122A and 122B of patient 120. For example, objects 320A and 320B may be virtual objects. Objects 330A and 330B may be real objects (e.g., physical objects). For example, diagnostic system 110 may permit light reflected from objects 330A and 330B to be transferred to one or more eyes 122A and 122B of patient 120.

Diagnostic system 110 may configure a distance to a virtual object 320 utilizing optics of diagnostic system 110. For example, diagnostic system 110 may configure a distance to a virtual object 320 utilizing one or more of projector 230, lens 220, deformable mirror 224, and lens 226, among others. Diagnostic system 110 may determine measurements associated with an eye 122 while an object is at a configured distance. In one example, diagnostic system 110 may configure a first distance to a virtual object 320 (e.g., a distance 340 illustrated in FIG. 3B) and may determine first measurements associated with eye 122. In a second example, diagnostic system 110 may configure a second distance, which may be different from the first distance, to virtual object 320 (e.g., a distance 342 illustrated in FIG. 3C) and may determine second measurements associated with eye 122.

Figure 3B:
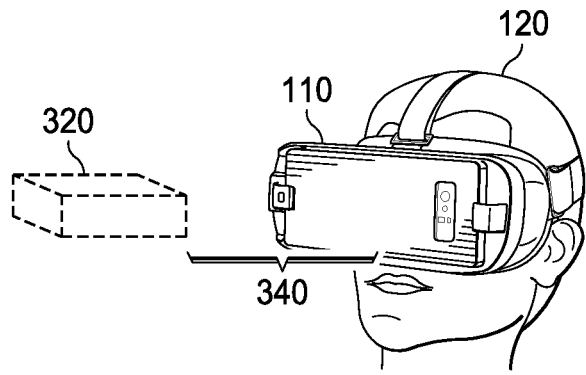
FIG. 3B illustrates an example of displaying a virtual object at a first distance.
Figure 3C:
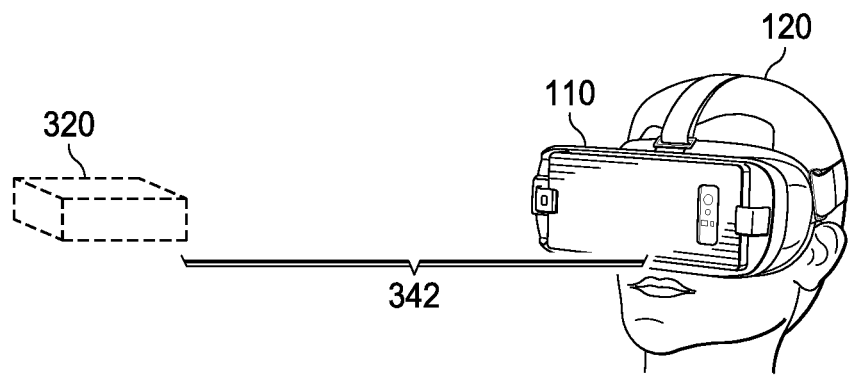
FIG. 3C illustrates an example of displaying a virtual object at a second distance.
Figure 3D:
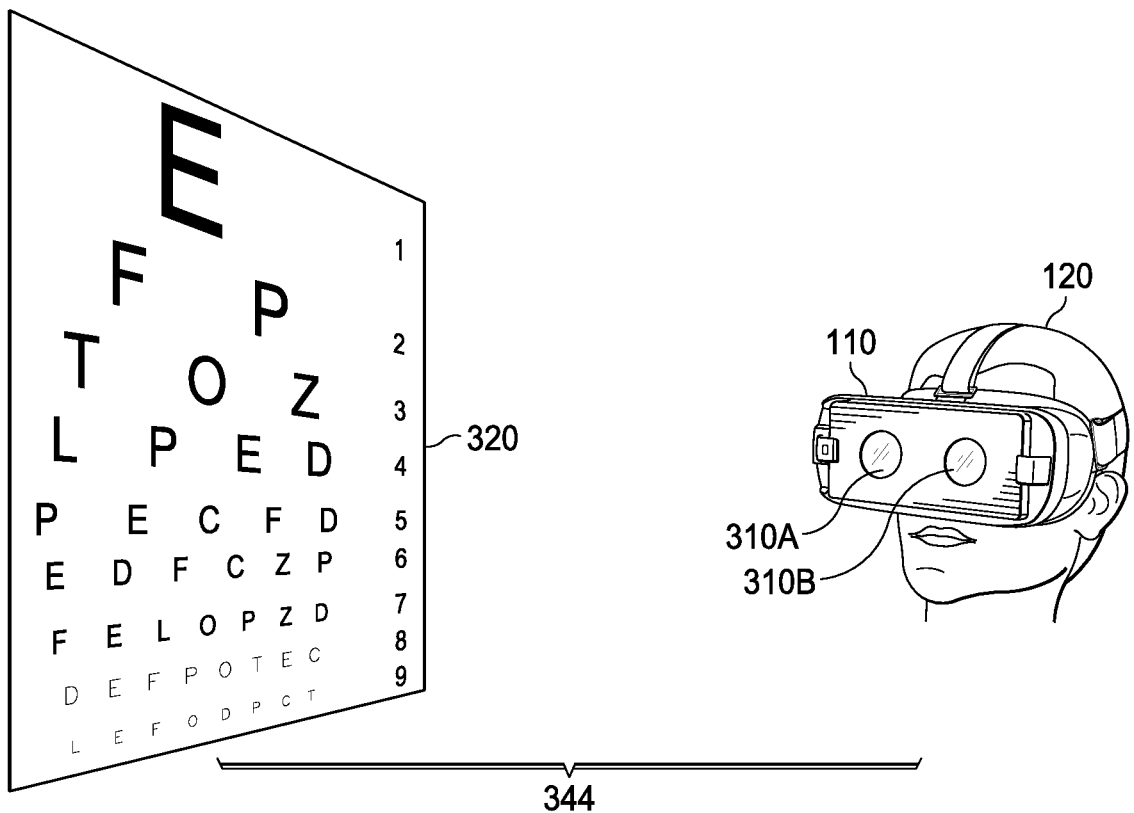
FIG. 3D illustrates an example of displaying a virtual object that includes a chart at a third distance.
Figure 3E:
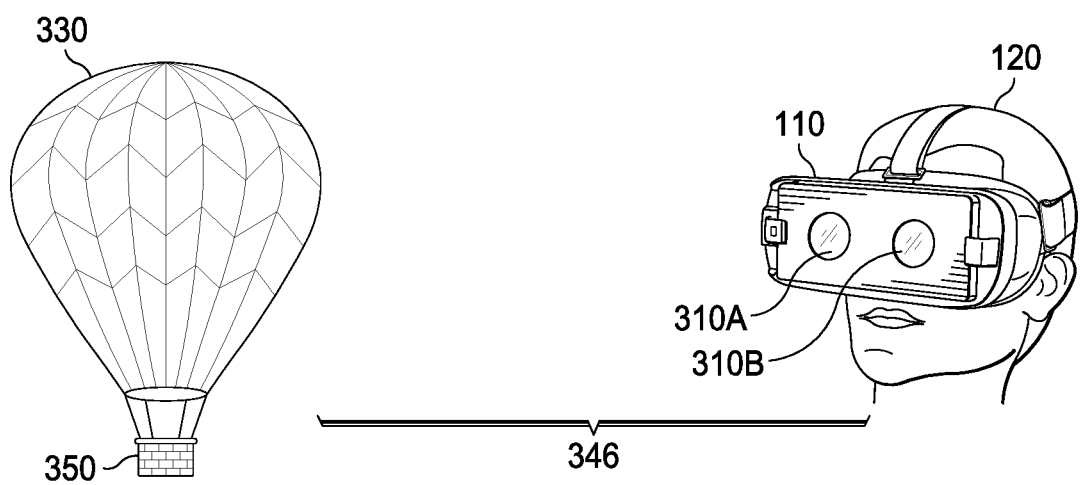
FIG. 3E illustrates an example a real object that includes a chart at a fourth distance.
Figure 3F:
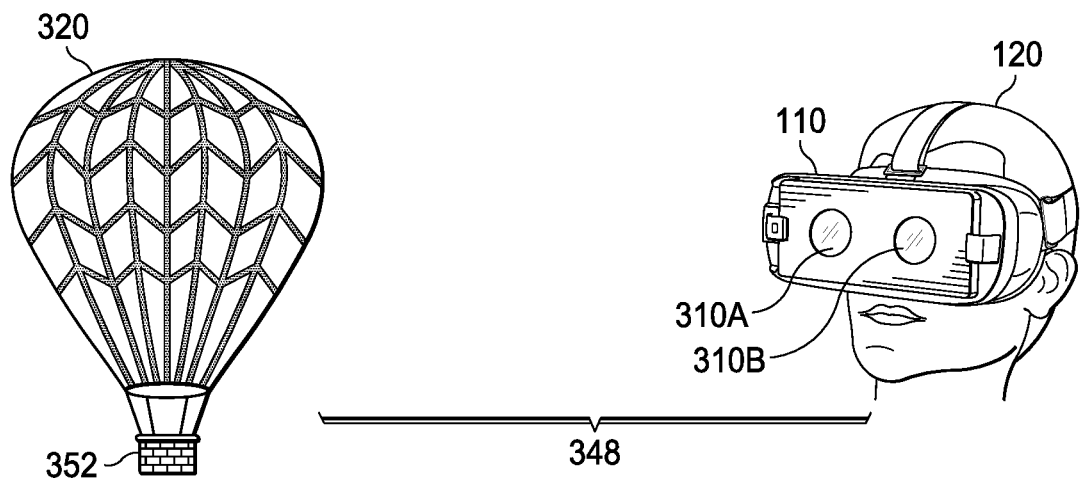
FIG. 3F illustrates an example of displaying a virtual object a fifth distance.

In a third example, diagnostic system 110 may provide a Snellen chart via virtual object 320 (e.g., at a distance 344 illustrated in FIG. 3D). Providing the Snellen chart via virtual object 320 may include providing the Snellen chart in three-dimensional space (e.g., three-dimensional virtual space). In a fourth example, a balloon may be provided via real object 330 (e.g., at a distance 346 illustrated in FIG. 3E). Real object 330 may be a real three-dimensional object (e.g., a physical three-dimensional object). Real object 330 may be a real two-dimensional picture (e.g., a physical two-dimensional picture). In a fifth example, diagnostic system 110 may provide a balloon chart via virtual object 320 (e.g., at a distance 348 illustrated in FIG. 3F). Virtual object 330 may be a virtual three-dimensional object. Virtual object 330 may be a two-dimensional picture. Two or more of distances 340-348 may be different distances. Two or more of distances 340-348 may be equal distances.

In a sixth example, diagnostic system 110 may configure a changing and decreasing distance to virtual object 320 and may determine third measurements associated with eye 122, as virtual object 320 appears to move closer to eye 122. In another example, diagnostic system 110 may configure a changing and increasing distance to virtual object 320 and may determine fourth measurements associated with eye 122, as virtual object 320 appears to move farther away from eye 122. Optics, of diagnostic system 110, in combination with virtual objects 320 may be utilized to simulate one or more customized refractive corrections. For example, the one or more customized refractive corrections may include a presbyopia correction, among others. Diagnostic system 110 may simulate an effect of multifocal corrections (e.g., near focus and/or far focus depending on a pupil size of eye 122). For example, the pupil size of eye 122 may include a diameter measurement of a pupil of eye 122. Optics of diagnostic system 110 may include adaptive optics.

Diagnostic system 110 may provide a virtual object 320 to an eye 122 based at least on one or more determined measurement associated with eye 122. For example, virtual object 320 may be altered based at least on the one or more determined measurement associated with eye 122. An altered virtual object 320 may appear as unaltered to eye 122. For example, diagnostic system 110 may alter virtual object 320 and may utilize optics of diagnostic system 110 to provide an altered virtual object 320 to eye 122 such that altered virtual object 320 may not appear to be altered to eye 122.

A resolution of a virtual object 320 may be limited by a pixel density of a projector 230. A resolution of an object 330 may not be limited by a pixel density of a projector 230. In one example, one or more virtual objects 320 and/or one or more real objects 330 may be utilized with one or more eyes 122A and 122B of patient 120. In another example, details of balloon basket 350 of real object 330 (illustrated in FIG. 3E) may be more pronounced and/or have a higher resolution than details of balloon basket 352 of virtual object 320 (illustrated in FIG. 3F). Diagnostic system 110 may include a mixed reality system that may utilize one or more virtual objects 320 and/or one or more real objects 330.

A resolution of a virtual object 320 may be changed. For example, a resolution of a virtual object 320 may be reduced. A color of a virtual object 320 may be changed. For example, a color of a virtual object 320 may be changed from a first color to a second color, different from the first color. A brightness of a virtual object 320 may be changed. For example, a brightness of a virtual object 320 may be changed from a first brightness to a second brightness, different from the first brightness.

A contrast of a virtual object 320 may be changed. For example, a contrast of a virtual object 320 may be changed from a first contrast to a second contrast, different from the first contrast. Changing a contrast of a virtual object 320 may include changing a brightness of a background of virtual object 320. For example, a brightness of a background of a virtual object 320 may be changed from a first brightness to a second brightness, different from the first brightness. A color of a background of a virtual object 320 may be changed. For example, a color of a background of a virtual object 320 may be changed from a first color to a second color, different from the first color.

Figure 4:
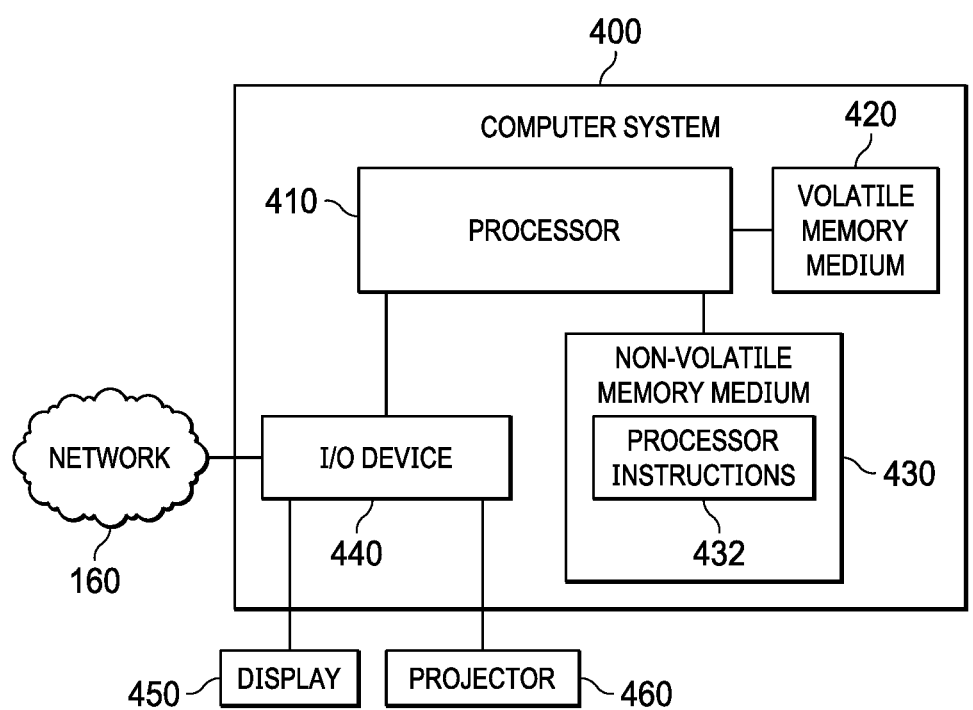
FIG. 4 illustrates an example of a computer system.

Turning now to FIG. 4, an example of a computer system is illustrated. As shown, a computer system 400 may include a processor 410, a volatile memory medium 420, a non-volatile memory medium 430, and an input/output (I/O) device 440. As illustrated, volatile memory medium 420, non-volatile memory medium 430, and I/O device 440 may be communicatively coupled to processor 410.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 430 may include processor instructions 432. Processor instructions 432 may be executed by processor 410. In one example, one or more portions of processor instructions 432 may be executed via non-volatile memory medium 430. In another example, one or more portions of processor instructions 432 may be executed via volatile memory medium 420. One or more portions of processor instructions 432 may be transferred to volatile memory medium 420.

Processor 410 may execute processor instructions 432 in implementing at least a portion of one or more systems, one or more flow charts, one or more processes, and/or one or more methods described herein. For example, processor instructions 432 may be configured, coded, and/or encoded with instructions in accordance with at least a portion of one or more systems, one or more flowcharts, one or more methods, and/or one or more processes described herein. Although processor 410 is illustrated as a single processor, processor 410 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 410 may include any suitable system, device, or apparatus operable to interpret and execute program instructions, process data, or both stored in a memory medium and/or received via a network. Processor 410 further may include one or more microprocessors, microcontrollers, digital signal processors (DSPs), application specific integrated circuits (ASICs), or other circuitry configured to interpret and execute program instructions, process data, or both.

I/O device 440 may include any instrumentality or instrumentalities, which allow, permit, and/or enable a user to interact with computer system 400 and its associated components by facilitating input from a user and output to a user. Facilitating input from a user may allow the user to manipulate and/or control computer system 400, and facilitating output to a user may allow computer system 400 to indicate effects of the user's manipulation and/or control. For example, I/O device 440 may allow a user to input data, instructions, or both into computer system 400, and otherwise manipulate and/or control computer system 400 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 440 may include one or more busses, one or more serial devices, and/or one or more network interfaces, among others, that may facilitate and/or permit processor 410 to implement at least a portions of one or more systems, processes, and/or methods described herein. In one example, I/O device 440 may include a storage interface that may facilitate and/or permit processor 410 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 440 may include a network interface that may facilitate and/or permit processor 410 to communicate with a network. I/O device 440 may include one or more of a wireless network interface and a wired network interface. In a third example, I/O device 440 may include one or more of a peripheral component interconnect (PCI) interface, a PCI Express (PCIe) interface, a serial peripheral interconnect (SPI) interface, and an inter-integrated circuit (I²C) interface, among others. In a fourth example, I/O device 440 may include circuitry that may permit processor 410 to communicate data with one or more sensors. In another example, I/O device 440 may facilitate and/or permit processor 410 to communicate data with display one or more of a display 450 and a projector 460, among others. As illustrated, I/O device 440 may be coupled to network 160. For example, I/O device 440 may include a network interface.

A computer system described herein may include one or more structures and/or one or more functionalities as those described with reference to computer system 400. In one example, computer system 130 may include one or more structures and/or one or more functionalities as those described with reference to computer system 400. In another example, computer system 210 may include one or more structures and/or one or more functionalities as those described with reference to computer system 400.

Figure 5A:
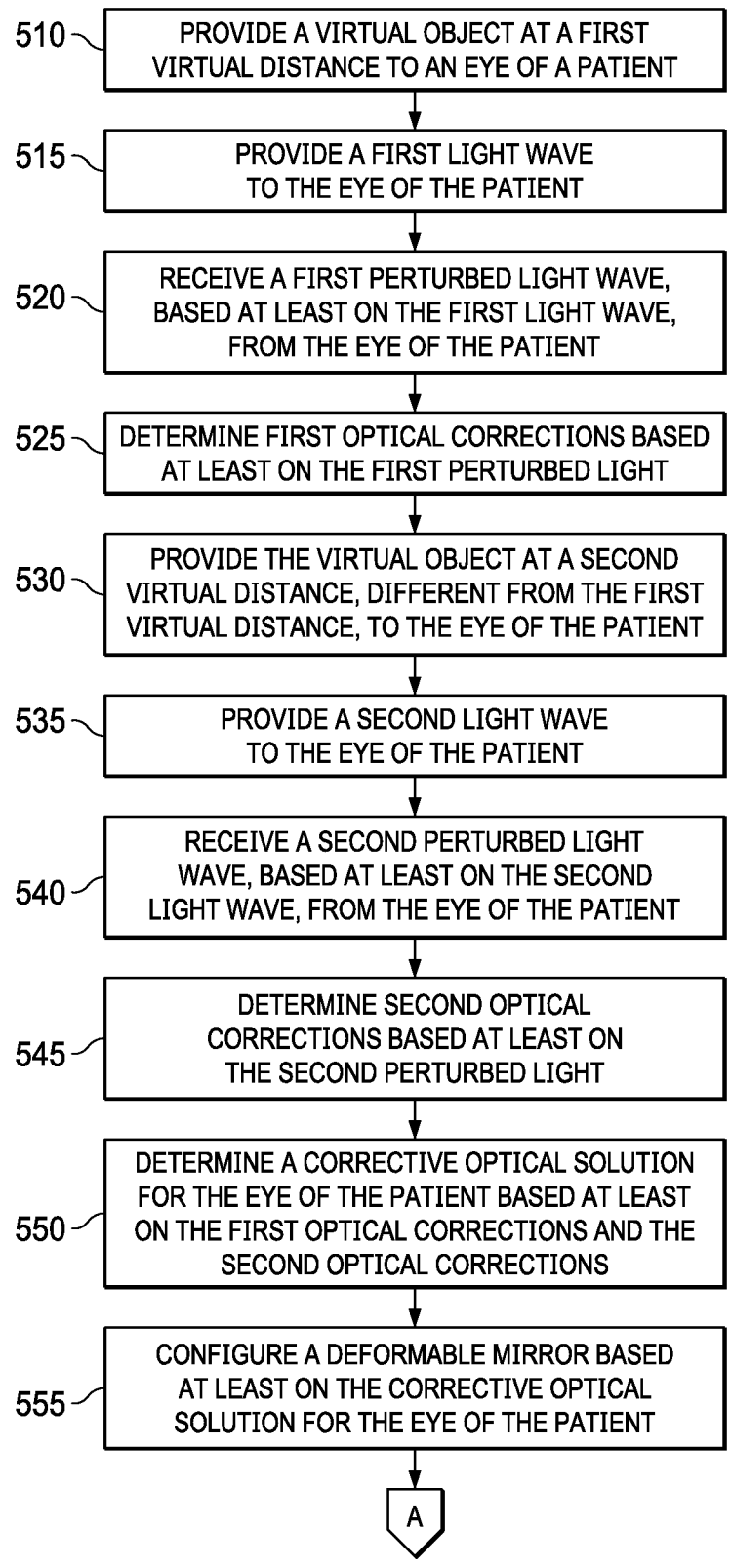
FIGS. 5A and 5B illustrate an example of a method of operating a system.
Figure 5B:
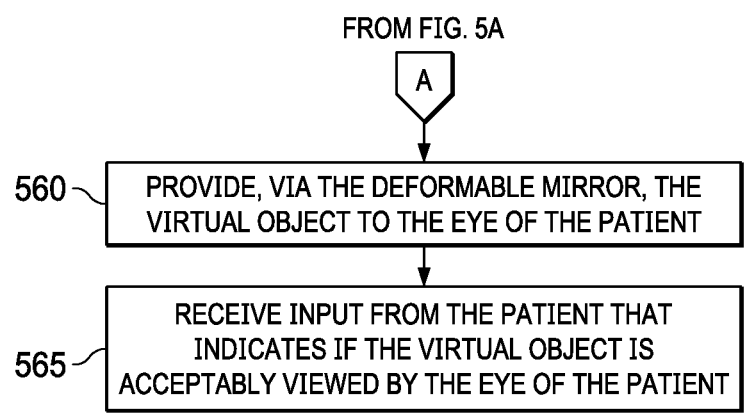

Turning now to FIGS. 5A and 5B, an example of a method of operating a diagnostic system is illustrated. At 510, a virtual object at a first virtual distance may be provided to an eye of a patient. For example, diagnostic system 110 may provide virtual object 320 at a first virtual distance 340, as illustrated in FIG. 3B, to an eye 122 of a patient 120. Providing a virtual object at a first virtual distance to an eye of a patient may include providing a simulation of a physical object at a first simulated physical distance to an eye of a patient. Before providing the virtual object at the first virtual distance to the eye of the patient, at least one lens may be adjusted. For example, at least one lens may be to provide the virtual object at the first virtual distance to the eye of the patient. At least one of lenses 226 and 220 may be adjusted to provide virtual object 320 at virtual distance 340 to eye 122. Adjusting a lens may include altering an angle of the lens. For example, altering an angle of the lens may include rotating the lens about an axis by a number of degrees or radians. Adjusting a lens may include altering a location of the lens.

At 515, a first light wave may be provided to the eye of the patient. For example, diagnostic system 110 may provide a first light wave to eye 122 of patient 120. Providing a first light wave to eye 122 of patient 120 may include light source 212 providing a first transmission of light 214 to eye 122.

At 520, a first perturbed light wave, based at least on the first light wave, may be received from the eye of the patient. For example, diagnostic system 110 may receive a first perturbed light wave, based at least on the first light wave, from eye 122. Receiving a first perturbed light wave, based at least on the first light wave, from the eye of the patient may include wavefront sensor 228 receiving a first perturbed light wave 222, based at least on the first transmission of light 214, from eye 122.

At 525, first optical corrections based at least on the first perturbed light may be determined. In one example, diagnostic system 110 may determine first optical corrections based at least on the first perturbed light. In another example, computer system 130 may determine first optical corrections based at least on the first perturbed light. Determining first optical corrections based at least on the first perturbed light may include determining first polynomials. For example, determining first polynomials may include determining first coefficients for polynomials.

At 530, the virtual object at a second virtual distance, different from the first virtual distance, may be provided to the eye of the patient. For example, diagnostic system 110 may provide virtual object 320 at a second virtual distance 342, as illustrated in FIG. 3C, to eye 122 of patient 120. Providing a virtual object at a second virtual distance to an eye of a patient may include providing a simulation of a physical object at a second simulated physical distance to an eye of a patient. Before providing the virtual object at the second virtual distance to the eye of the patient, at least one lens may be adjusted. For example, at least one lens may be to provide the virtual object at the second virtual distance to the eye of the patient. At least one of lenses 226 and 220 may be adjusted to provide virtual object 320 at virtual distance 342 to eye 122. Adjusting a lens may include altering an angle of the lens. For example, altering an angle of the lens may include rotating the lens about an axis by a number of degrees or radians. Adjusting a lens may include altering a location of the lens.

At 535, a second light wave may be provided to the eye of the patient. For example, diagnostic system 110 may provide a second light wave to eye 122 of patient 120. Providing a second light wave to eye 122 of patient 120 may include light source 212 providing a second transmission of light 214 to eye 122. Providing a second light wave to the eye of the patient may be performed after providing the virtual object at the second virtual distance, different from the first virtual distance, to the eye of the patient. For example, one or more structures and/or one or more elements of eye 122 may adjust to view the virtual object at the second virtual distance. Additional measurements associated with eye 122 may be acquired after the one or more structures and/or the one or more elements of eye 122 adjust to view the virtual object at the second virtual distance.

At 540, a second perturbed light wave, based at least on the second light wave, may be received from the eye of the patient. For example, diagnostic system 110 may receive a second perturbed light wave, based at least on the second light wave, from eye 122. Receiving a second perturbed light wave, based at least on the second light wave, from the eye of the patient may include wavefront sensor 228 receiving a second perturbed light wave 222, based at least on the second transmission of light 214, from eye 122.

At 545, second optical corrections based at least on the second perturbed light may be determined. In one example, diagnostic system 110 may determine second optical corrections based at least on the second perturbed light. In another example, computer system 130 may determine second optical corrections based at least on the second perturbed light. Determining second optical corrections based at least on the second perturbed light may include determining second polynomials. For example, determining second polynomials may include determining second coefficients for polynomials. The second polynomials may be different from the first polynomials. For example, a polynomial of the first polynomials may differ from a polynomial of the second polynomials by at least one coefficient value.

At 550, a corrective optical solution for the eye of the patient based at least on the first optical corrections and the second optical corrections may be determined. In one example, diagnostic system 110 may determine a corrective optical solution for the eye of the patient based at least on the first optical corrections and the second optical corrections. In another example, computer system 130 may determine a corrective optical solution for the eye of the patient based at least on the first optical corrections and the second optical corrections.

A corrective optical solution for the eye of the patient based at least on the first optical corrections and the second optical corrections may include a vision correction solution for eye 122. In one example, the corrective optical solution for eye 122 may include a corrective optical solution for refractive surgery of eye 122. In a second example, the corrective optical solution for eye 122 may include a corrective optical solution for an intraocular lens for eye 122. In a third example, the corrective optical solution for eye 122 may include a corrective optical solution for a contact lens for eye 122. In another example, the corrective optical solution for eye 122 may include a corrective optical solution for an external lens for eye 122 (e.g., a lens for glasses). The corrective optical solution for eye 122 may include polynomials. The corrective optical solution for eye 122 may include coefficients for polynomials. The corrective optical solution for eye 122 may include an aberration profile.

At 555, a deformable mirror may be configured based at least on the corrective optical solution for the eye of the patient. For example, diagnostic system 110 may configure deformable mirror 228 based at least on the corrective optical solution for eye 122.

Figure 2B:
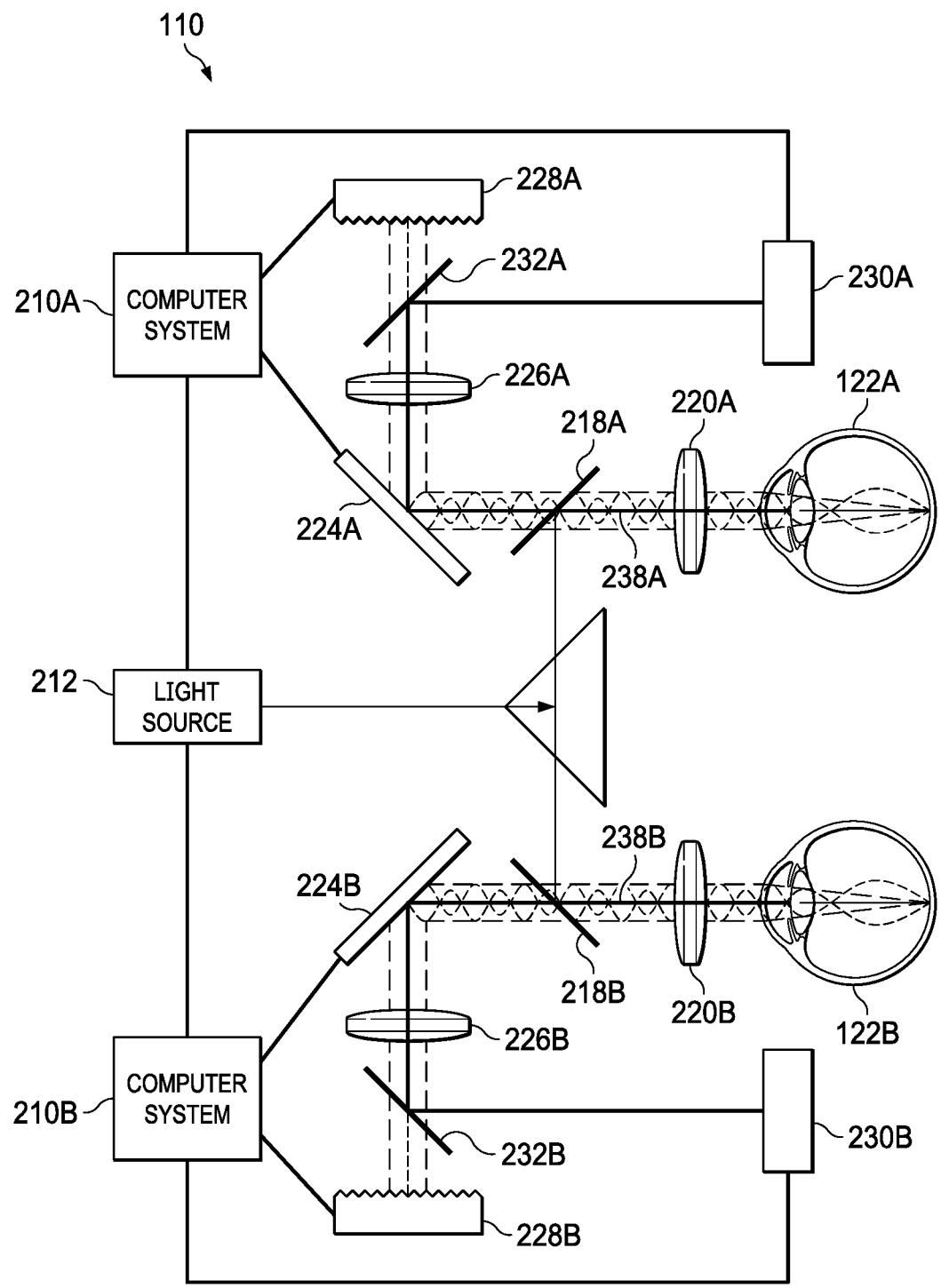
FIG. 2B illustrates an example of an optical path.

At 560, the virtual object to the eye of the patient via the deformable mirror. In one example, diagnostic system 110 may provide, via deformable mirror 228, the virtual object to eye 122. In another example, an optical path 238, illustrated in FIG. 2B, from projector 230 to eye 122 of patient 120 may include deformable mirror 224. Projector 230 may provide an image, associated with the virtual object, to deformable mirror 228. Deformable mirror may alter the image and provide an altered image to eye 122.

At 565, input from the patient that indicates if the virtual object is acceptably viewed by the eye of the patient may be received. In one example, diagnostic system 110 may receive input from patient 120 that indicates if virtual object 320 is acceptably viewed by eye 122. In another example, computer system 130 may receive input from patient 120 that indicates if virtual object 320 is acceptably viewed by eye 122. Receiving input from patient 120 may include receiving an actuation of a button. Receiving input from patient 120 may include determining motion of patient 120. For example, a sensor 236 may determine a motion of a head of patient 120, indicating if virtual object 320 is acceptably viewed by eye 122. Receiving input from patient 120 may include receiving an audio. For example, patient 120 may speak, indicating if virtual object 320 is acceptably viewed by eye 122. Receiving input from patient 120 if virtual object 320 is acceptably viewed by eye 122 may be utilized in determining if the corrective optical solution for eye 122 is correct and/or acceptable.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A system, comprising:
   at least one processor;
   a projector coupled to the at least one processor; and
   a memory medium that is coupled to the at least one processor and that includes instructions, when executed by the at least one processor, cause the system to:
   provide, via the projector, a virtual object at a first virtual distance to an eye of a patient;
   provide a first light wave to the eye of the patient;
   receive a first perturbed light wave, based at least on the first light wave, from the eye of the patient;
   determine first optical corrections based at least on the first perturbed light;
   provide, via the projector, the virtual object at a second virtual distance, different from the first virtual distance, to the eye of the patient;
   after providing the virtual object at the second virtual distance to the eye of the patient, provide a second light wave to the eye of the patient;
   receive a second perturbed light wave, based at least on the second light wave, from the eye of the patient;
   determine second optical corrections based at least on the second perturbed light; and
   determine a corrective optical solution for the eye of the patient based at least on the first optical corrections and the second optical corrections.

2. The system of claim 1, further comprising:
   a wavefront sensor coupled to the at least one processor;
   wherein, to receive the first perturbed light wave from the eye of the patient, the instructions further cause the system to receive the first perturbed light wave from the eye of the patient via the wavefront sensor; and
   wherein, to receive the second perturbed light wave from the eye of the patient, the instructions further cause the system to receive the second perturbed light wave from the eye of the patient via the wavefront sensor.

3. The system of claim 1, further comprising:
   a deformable mirror coupled to the at least one processor;
   wherein the instructions further cause the system to:
   configure the deformable mirror based at least on the corrective optical solution for the eye of the patient;
   provide, via the deformable mirror, the virtual object to the eye of the patient; and
   receive input from the patient that indicates if the virtual object is acceptably viewed by the eye of the patient.

4. The system of claim 3, wherein an optical path from the projector to the eye of the patient includes the deformable mirror.

5. The system of claim 1,
   wherein, to determine the first optical corrections based at least on the first perturbed light, the instructions further cause the system to determine a first plurality of polynomials based at least on the first perturbed light; and
   wherein, to determine the second optical corrections based at least on the second perturbed light, the instructions further cause the system to determine a second plurality of polynomials, different from the first plurality of polynomials, based at least on the second perturbed light.

6. The system of claim 5, wherein a polynomial of the first plurality of polynomials differs from a polynomial of the second plurality of polynomials by at least one coefficient value.

7. The system of claim 1, further comprising:
at least one lens;
wherein the instructions further cause the system to:
before providing the virtual object at the second virtual distance to the eye of the patient, adjust the at least one lens to provide the virtual object at the second virtual distance to the eye of the patient.

8. At least one non-transitory computer readable storage medium that includes instructions that, when executed by at least one processor of a system, cause the system to:
provide a virtual object at a first virtual distance to an eye of a patient;
provide a first light wave to the eye of the patient;
receive a first perturbed light wave, based at least on the first light wave, from the eye of the patient;
determine first optical corrections based at least on the first perturbed light;
provide the virtual object at a second virtual distance, different from the first virtual distance, to the eye of the patient;
after providing the virtual object at the second virtual distance to the eye of the patient, provide a second light wave to the eye of the patient;
receive a second perturbed light wave, based at least on the second light wave, from the eye of the patient;
determine second optical corrections based at least on the second perturbed light; and
determine a corrective optical solution for the eye of the patient based at least on the first optical corrections and the second optical corrections.

9. The at least one non-transitory computer readable storage medium of claim 8,
wherein, to receive the first perturbed light wave from the eye of the patient, the instructions further cause the system to receive the first perturbed light wave from the eye of the patient via a wavefront sensor; and
wherein, to receive the second perturbed light wave from the eye of the patient, the instructions further cause the system to receive the second perturbed light wave from the eye of the patient via the wavefront sensor.

10. The at least one non-transitory computer readable storage medium of claim 8, wherein the instructions further cause the system to:
configure a deformable mirror based at least on the corrective optical solution for the eye of the patient;
provide, via the deformable mirror, the virtual object to the eye of the patient; and
receive input from the patient that indicates if the virtual object is acceptably viewed by the eye of the patient.

11. The at least one non-transitory computer readable storage medium of claim 10, wherein an optical path from a projector, that provides the virtual object, to the eye of the patient includes the deformable mirror.

12. The at least one non-transitory computer readable storage medium of claim 8,
wherein, to determine the first optical corrections based at least on the first perturbed light, the instructions further cause the system to determine a first plurality of polynomials based at least on the first perturbed light; and
wherein, to determine the second optical corrections based at least on the second perturbed light, the instructions further cause the system to determine a second plurality of polynomials, different from the first plurality of polynomials, based at least on the second perturbed light.

13. The at least one non-transitory computer readable storage medium of claim 12, wherein a polynomial of the first plurality of polynomials differs from a polynomial of the second plurality of polynomials by at least one coefficient value.

14. A method, comprising:
providing a virtual object at a first virtual distance to an eye of a patient;
providing a first light wave to the eye of the patient;
receiving a first perturbed light wave, based at least on the first light wave, from the eye of the patient;
determining first optical corrections based at least on the first perturbed light;
providing the virtual object at a second virtual distance, different from the first virtual distance, to the eye of the patient;
after the providing the virtual object at the second virtual distance to the eye of the patient, providing a second light wave to the eye of the patient;
receiving a second perturbed light wave, based at least on the second light wave, from the eye of the patient;
determining second optical corrections based at least on the second perturbed light; and
determining a corrective optical solution for the eye of the patient based at least on the first optical corrections and the second optical corrections.

15. The method of claim 14,
wherein the receiving the first perturbed light wave, based at least on the first light wave, from the eye of the patient includes a wavefront sensor receiving the first perturbed light wave, based at least on the first light wave, from the eye of the patient; and
wherein the receiving the second perturbed light wave, based at least on the first light wave, from the eye of the patient includes a wavefront sensor receiving the second perturbed light wave, based at least on the second light wave, from the eye of the patient.

16. The method of claim 14, further comprising:
configuring a deformable mirror based at least on the corrective optical solution for the eye of the patient;
providing the virtual object to the eye of the patient; and
receiving input from the patient that indicates if the virtual object is acceptably viewed by the eye of the patient.

17. The method of claim 16, wherein an optical path from a projector that provides the virtual object to the eye of the patient includes the deformable mirror.

18. The method of claim 14,
wherein the determining the first optical corrections based at least on the first perturbed light includes determining a first plurality of polynomials based at least on the first perturbed light; and
wherein the determining the second optical corrections based at least on the second perturbed light includes determining a second plurality of polynomials, different from the first plurality of polynomials, based at least on the second perturbed light.

19. The method of claim 18, wherein a polynomial of the first plurality of polynomials differs from a polynomial of the second plurality of polynomials by at least one coefficient value.

20. The method of claim 14, further comprising:
before the providing the virtual object at the second virtual distance to the eye of the patient, adjusting at least one lens to provide the virtual object at the second virtual distance to the eye of the patient.

\* \* \* \* \*